United States Patent [19]

Pouletty

[11] Patent Number: 5,292,641
[45] Date of Patent: Mar. 8, 1994

[54] ALLOANTIGEN TESTING BY BINDING ASSAY

[75] Inventor: Philippe Pouletty, Atherton, Calif.

[73] Assignee: SangStat Medical Corporation, Menlo Park, Calif.

[21] Appl. No.: 807,287

[22] Filed: Dec. 13, 1991

[51] Int. Cl.$^5$ .......................................... G01N 33/543
[52] U.S. Cl. ................................. 435/7.24; 435/7.92; 435/7.93; 436/518
[58] Field of Search .................... 435/7.21, 7.24, 7.25, 435/7.92, 7.93; 436/518, 533, 534

[56] References Cited

U.S. PATENT DOCUMENTS

| | | | |
|---|---|---|---|
| 3,654,090 | 4/1972 | Schuurs et al. | 436/518 |
| 4,446,239 | 5/1984 | Tsuji et al. | 436/517 |
| 4,607,009 | 8/1986 | Steplewski et al. | 435/7.25 |
| 5,110,726 | 5/1992 | Ogden | 435/7.21 |
| 5,132,209 | 7/1992 | Vanderbeeken | 435/7.21 |

OTHER PUBLICATIONS

Y. Iwaki, et al., (1988) Clinical Transplantation 2:81–84. Successful transplants across T warm–positive crossmatches due to IgM antibodies.
Grosse-Wilde and Doxiadis (1989) J. Immunogenetics 16:149–155. Allotyping forHLA Class I using plasma as antigen source.
F. Stevenson, et al. (1986) J. Imm. Methods 86:187–190. Analysis of soluble HLA Class II antigenic material in patients with immunological disease using monoclonal antibodies.
D. Talbot, et al. (1988) J. Imm. Methods 112:279–283. Rapid detection of lowlevels of donor specific IgG by flow cytometry with single and dual colour fluorescence in renal transplantation.
R. Duquesnoy, et al. (1990) Transplantation 50:427–437. Mutiscreen serum analysis of highly sensitized renal dialysis patients for antibodies toward public and private Class I HLA determinants.
S. Martin, et al. (1987) Transplantation 50:427–437. Posttransplant antidonor lymphocytotoxic antibody production in relation to graft outcome.
R. Tsuji, et al. (1985) Tokai J. Exp. Clin. Med. 10:169–174. Biological significance of Ss (serum soluble) HLA-Class I antigens in bone marrow transplantation.
R. Fauchet, et al. (1989) Transplantation 30:114–129. Occurance and specificity of anti-B lymphocyte antibodies in renal allograft recipients.
H. Davies, et al. (1989) Transplantation 47:524–527. Soluble HLA antigens in the circulation of liver graft recipients.
Doxiadis and Grosse-Wilde (1989) Vox Sang 56:196–199. Typing for HLA Class I gene products using plasma as source.
B. R. Clark et al, in E. T. Maggio (ed), *Enzyme Immunoassay*, CRC Press, Boca Raton, FL, 1980, pp. 167–170.
Immucor Advertisement of Oct. 20, 1986.

*Primary Examiner*—David Saunders
*Attorney, Agent, or Firm*—Rowland, Bertram I.

[57] ABSTRACT

The presence of alloantigen allelic products or antibodies to alloantigen allelic products is determined by employing a support to which alloantigen allelic products are bound, and combining a specimen which contains either the alloantigen allelic products or antibodies to alloantigen allelic products with a reagent comprising antibodies to the alloantigen allelic product(s) of interest. By combining the specimen, reagent and support, and determining the amount of antibody which binds to the support as compared to a negative control, the presence of the alloantigen antigen or anti-alloantigen is related to a reduced amount of antibody binding to the support. The amount of antibody may be determined by any convenient assay.

4 Claims, No Drawings

ALLOANTIGEN TESTING BY BINDING ASSAY

INTRODUCTION

1. Technical Field

The field of this invention is the detection of reactivity between alloantigen and alloantigen-specific ligand in biological samples.

2. Background

In many transplantation-type situations, there is concern for differences between the allotype, especially the HLA type, of a cell source and the cell recipient. In situations where allogenic cells or tissue are taken from a donor and introduced into a recipient, it is desirable that the donor and recipient be as closely HLA matched as possible. The presence in the patient serum of antibodies against HLA antigens of the donor (donor specific crossmatch) or against a high percentage of HLA alleles (PRA testing) predicts a high risk of graft rejection.

The determination of HLA phenotype (HLA typing) is useful in numerous situations such as transplantation, platelet transfusion and forensic or paternity testing. The standard technique for HLA typing and detection of anti-HLA antibodies is microlymphocytotoxicity, where serum containing antibodies is incubated with HLA antigen-expressing lymphocytes, then with complement. The level of cytotoxicity is then estimated by discriminating between dead and viable cells using various dyes. This method has numerous disadvantages: it is labor intensive; time consuming; requires isolation of cells; requires viable cells; is nonspecific for HLA; and requires a subjective evaluation. Flow cytometry may also be used but requires a large number of cells and expensive instrumentation.

It is therefore of interest to provide alternative techniques which can be performed simply, can be automated, do not share the shortcomings described above, and provide a readily discernible result which is significant for the prognosis of graft acceptance.

Relevant Literature

References of interest include Duquesnoy et al. (1990) *Transplantation* 50:427–437; Martin et al. (1987) *Transplantation* 44:50–53; Grosse-Wilde et al. (1989) *J. Immunogenet.* 16:149–55; Doxiadis et al. (1969) 59:449–54; Doxiadis and Grosse-Wilde (1989) *Vox Sang* 56:196–99; Davies et al. (1989) *Transplantation* 47:524–27; Tsuji et al. (1985) Tokai *J. ExD. Clin Med.* 10:169–74; Stevenson et al. (1986) *J. Immunol. Methods* 86:187–90; Fauchet et al. (1989) *Transplantation* 30:114–129; Talbot et al. (1988) *J. Immunol. Methods* 112:279–83; Iwaki et al. (1988) *Clin. Transplantation* 2:81–84.

SUMMARY OF THE INVENTION

HLA/anti-HLA ligand reactivity is determined by combining (a) a solid support prepared by immobilizing on a solid phase, at least one HLA antigen or binding portion thereof; (b) a specimen, which either contains anti-HLA or HLA antigen; and (c) a reagent composition comprising the competitive or reciprocal binding member. Reduced binding of antibodies as compared to a standard is a measure of the presence of antibodies in the specimen or the presence of a particular HLA-allele composition in the specimen.

DESCRIPTION OF THE SPECIFIC EMBODIMENTS

In accordance with the subject invention, a simple rapid and accurate method is provided for the determination of the presence of at least one particular HLA allele or the presence of antibodies to at least one HLA allele. the method involves having one or more known HLA antigens or binding fragments thereof bound to a surface. Depending upon what is assayed, either antibodies to one or more HLA antigens or platelets, white blood cells, or the like, or soluble HLA antigens, namely dispersible HLA antigens, the specimen is combined with the reciprocal binding member. One then measures the amount of antibody which becomes bound to the surface by any convenient means, either as indicative of the presence of specific antibodies in the specimen, which bind to the known support bound allele(s) or indicative of particular HLA antigens in the specimen Any means may be employed for detecting the presence of antibody bound to the support.

A wide variety of specimens may be used, where one is interested in the presence of either antibodies or alloantigens e.g. HLA antigens. Embodiments of this invention find use in identifying antibodies to known histocompatibility antigens (crossmatching), identifying histocompatibility antigens with antibodies of known specificities (HLA typing), or identifying general alloreactivity toward a panel of histocompatibility antigens (Panel Reactive Antibody testing, PRA). For the purposes of the subject invention, an alloantigen is a direct or indirect product of an allele of a species which may be detected as an antigen by another member of the same species, particularly where the allele is an HLA antigen. The HLA antigens may be Class I, II or the minor histocompatibility antigen group. Other alloantigens include those related to red blood cells and the like. (In referring to HLA antigens, it is understood that any major histocompatibility complex antigen or antibody thereto may be detected.)

The specimens which are employed may include, serum, plasma, whole blood, cells, e.g. white blood cells or platelets, saliva, cerebrospinal fluid, other tissues or cells, depending upon whether the analyte of interest is the HLA antigen or the antibody.

The antibody reagent employed as the competitive or complementary binding material may include monoclonal antibodies or alloantisera, neat, diluted or affinity purified antisera, which may be specific for one or more alleles of interest. The concentration of the antibody will be adjusted so that it is not in such excess as to prevent the occurrence of an inhibition of binding to the solid phase by the minimum amount of alloantigen which needs to be detected This can be readily determined by employing serial dilution with standards. Alternatively, one may use a inhibitor of the specimen and/or reagent to define the progress ratio; usually the dilution will be from about 1:5–1:1000.

Since the measured value is a reduced amount of antibody reagent being bound to the support as a result of the presence of HLA antigen or alloantiserum in the specimen, one is primarily interested in a sufficient differential in amount of immunoglobulin bound to the support to provide for a detectable level, and, as appropriate, a quantitative determination. Thus, the amount of HLA antigen bound to the support for detection of soluble HLA antigen will usually have binding sites in substantial excess to the amount of immunoglobulin binding sites for the antigen present in the assay medium and for the amount of immunoglobulin reagents.

For the reagent for the competitive assay, the amount of HLA antigen on the support will be limited in relation to the amount of reagent employed. The HLA-antigen bound to the support and antibody reagent in the assay medium will be selected to provide a detectable response in the presence of alloantisera of the HLA-antigen on the support. One or more monoclonal antibodies may be mixed, where there is interest in the presence or absence of one or a plurality of HLA antigens, alloantiserum of known specificity may be employed, affinity purified alloantiserum may be employed, or the like.

The positive result of an HLA-antigen being present or antisera to an HLA-antigen will be reduced binding of the immunoglobulin reagent to the support. This will be indicative of the presence of the HLA antigen allele(s) of interest or antibodies to such allele(s) in the specimen. For a particular HLA-allele(s), or antibodies thereto, one may use the same reagent.

The alleles bound to the support may be derived from any convenient source, depending upon the nature of the HLA allele of interest, Class I, II or minor histocompatibility antigen group. Thus, the antigens may be derived from human donors, including platelets, plasma, serum or renal dialysis derivatives, lymphoblastoid cell lines (or hybridomas derived therefrom), transfectant cell lines, or any other convenient source of the desired antigen repertoire. Mixtures from different embodiments can be used to provide a universal support, carrying all of the popular allelic proteins. The antigens may be bound to the support in accordance with known techniques, depending upon the nature of the support. Binding may be covalent or non-covalent, being non-diffusibly bound. The support may be any convenient solid support, which may include container walls or bottoms, e.g. microtiter plate wells, test tubes, beads, slides, absorbent films, membranes, particles, e.g. magnetic particles, or the like. The particular support is not critical, and any support may be used, where non-specific binding may be minimized, where the support does not interfere with the measurement, and where the support allows for a convenient protocol. A large number of solid supports are known, which are activated, and will form covalent bonds with proteins. Other supports are known, where the support may be activated by adding reagents, resulting in reaction with proteins. In addition, in some instances, mild heating will provide for non-diffusible binding of proteins to the support. The support may include glass, plastics, e.g. polystyrene, polyacrylate, polyethylene, polypropylene, etc., cellulose, e.g. paper, nitrocellulose, cellulose acetate, etc., and the like.

After binding the antigens to the support, a blocking group may conveniently will be added, conveniently an innocuous protein for reacting with any active sites, or a detergent, so as to reduce non-specific binding. Numerous blocking materials have been employed, such as milk, bovine serum albumin, $\beta$-globin, Tween 20, etc.

Once the solid support has been prepared, the specimen and immunoglobulin reagent may be combined. The specimen may have been subject to prior treatment, such as dilution, removal of interfering materials, e.g. red blood cells, coagulating agents, and the like. The specimen, which will generally be from about 1 $\mu$l to 0.5 ml may then be combined with the reagent. As indicated, the reagent may be a solution of one or more monoclonal antibodies or alloantisera having known specificity. The amount of antibodies present will be selected, so as to be capable of measurement when bound to the support. The amount will be chosen so as to ensure that the level of HLA antigen or anti(HLA antigen) in the specimen will be sufficient to provide for discrimination between the presence and absence of the particular allele(s) or antisera.

The specimen and reagent will normally be combined prior to combining with the solid support, although the specimen, reagent and solid support may be combined simultaneously or the specimen may be first added to the solid support, or the antibody may be added first, depending upon the protocol and what is being measured. The assay medium will usually be buffered with an appropriate buffer, at a pH in the range of about 5-10. The buffer may be phosphate, carbonate, Hepes, Mops, Tris, or the like. Generally, the buffer concentration will be sufficient to maintain the desired pH, usually being at least 15 mM and not more than about 500 mM. Other additives may be present in minor amounts, such as innocuous proteins, generally not exceeding about 15%, stabilizing agents, e.g. azide, etc.

The mixture may be incubated for sufficient time for reaction to occur at each stage. Usually, incubation times range from about 1 min. to 180 mins., more usually from about 5 min. to 30 min., except when a flow-through device is used where the time may be shorter. After sufficient time for binding to the support, the support may be washed by any convenient means, using water or a buffered medium, generally at a pH in the range of about 5-10 and having from about 10-500 mM of the buffering agent. One or more washes may be employed to ensure substantial removal of any non-specific binding.

After the incubation washings, the amount of antibody bound to the surface may be determined. Any technique for determining antibody bound to the surface may be employed, which may or may not include an additional detection molecule. There are a large number of reagents which bind to antibodies. One may use anti-human antibodies, protein A, Fc receptor, etc. The antibody reagents, particularly anti-HLA antibody, may be labelled, so as to be directly detectable. Labels may include dyes, fluorescers, enzymes, chemiluminescers, particles, radioisotopes, biotin to bind to labeled avidin, or other detectable agent. With the enzymes, various substrates may be employed, which provide for light absorption, fluorescence, chemiluminescence, or the like. The particular label is not critical to this invention and is primarily a matter of convenience. In the case of an enzyme label, the reaction will usually be timed and terminated in accordance with any convenient means.

Assay techniques for measuring human antibody may include ELISA, FIA, RIA or the like, where the labeled reagent specifically binds to the human antibody.

Normally, a negative control assay will be carried out, where the specimen will be replaced with buffer or buffer containing innocuous antibodies or other medium which mimics the nature of the specimen, e.g. a nutrient medium, cell culture supernatant, etc. Thus, the control test will generally mimic, as closely as possible, the specimen assay. Normally, multiple controls will be used to provide for a base and a standard deviation, so that usually two standard deviations will be employed as being the baseline for a positive result.

Various protocols other than the protocols described above may be employed, depending upon the materials and devices employed and available. For example, an agglutination format may be employed, where alloantigens are bound to beads, e.g. latex beads, generally of from about 10µ to 100µ diameter, so that the beads are coated with at least the most popular antigens, preferably substantially all of the class of interest. The ratio of beads to specimen is selected, e.g. by serial dilution, to detect the presence of antibodies to the alloantigen(s) on the beads.

In the next test, two unknowns are present, where one is interested in cross-matching, e.g. blood, usually as serum from a transplant donor being matched with blood serum from a transplant recipient. In this format, one would perform the assay with the candidate blood, e.g. the recipient blood to demonstrate the presence or absence of binding to the HLA antigens on the beads. And, one would perform the same assay in the presence of donor specimen, e.g. cells, soluble HLA in serum, etc. The beads would be conjugated with a plurality of HLA antigens, for example, from a cross-section of individuals, selected HLA antigens providing a cross-section of common HLA antigens, or the like. If no agglutination is observed in the latter case, there are no anti-HLA antibodies. Binding in the absence of donor specimen indicates the presence of anti-HLA antibodies and a positive PRA. In the presence of the donor specimen, a reduction of binding indicates a positive cross-match, while the absence of any reduction indicates a negative cross-match. In this manner, one can determine the reactivity of a candidate serum and cross-match, with two unknowns being analyzed simultaneously or separately.

The reagents for the subject invention can be provided in a kit. The kit would include the HLA antigens bound to the support, control solutions, and the reagents necessary for -the determination, which as already indicated, could be reagents for an enzyme immunoassay, radioimmunoassay, fluorescence immunoassay, or chemiluminescent immunoassay. Other reagents which may be present include buffer, which may be appropriately diluted, substrates, in the case of an enzyme immunoassay, stop solution to stop color development, software program to record and/or analyze the results and the and the allele specificities. The results may be determined in accordance with the nature of the assay, using a spectrophotometer, fluorimeter, scintillation counter, reflectometer, luminometer, etc.

The subject method has numerous advantages, in being able to use alloantisera, permits rapid typing of numerous alleles, allows quantitative objective reading of results, has a simple protocol and can employ a wide variety of reagents, which are readily available.

The following examples are offered by way of illustration and not by way of limitation.

EXPERIMENTAL

Materials

-alloantiserum #939 specimen (titer 1:8 and anti-B7 by microlymphocytotoxicity)
-inhibitor=supernatant from lymphoblastoid cell line (Ref 7666, phenotype: HLA A3, Aw29, B7, B12 by microlymphocytotoxicity, 0.50 µg/ml of total HLA Class I, as measured by sHLA-STAT ™ Class 1 ELISA [SangStat Medical Corp.], cultured in RPMI 1640 20% FBS)

Nunc plates coated using HLA antigen [derived from a pool of 60 random platelet donors; extracted from platelet using detergent (NP40) followed by differential centrifugation and affinity chromatography (using HLA Class I specific monoclonal antibody W6.32)]

Coating by incubating 100 µl per well of HLA antigen (2.5 µg/ml in PBS pH 7.4 overnight at 4° C.; Wells were blocked by 250 µl per well of PBS containing 1% casein and 0.05% Tween 20 (4 hours at room temperature).

STUDY 1

The assay was run as follows:

1. Dilute the human serum specimen into inhibitor, i.e. either supernatant from lymphoblastoid cell line (Ref 7666, 0.5 µg/mL) or RPMI 1640 20% FBS (negative control):

| SERUM FINAL DILUTION | SERUM/INHIBITOR RATIO (Vol/Vol, µl) |
|---|---|
| 1/2 | 110:110 |
| 1/10 | 25:225 |
| 1/100 | 5:495 |

2. Mix serum and antigen thoroughly and incubate at RT for 15 minutes.

3. Pipet 100 µl of the mixture into duplicate wells of an HLA-coated plate and incubate at 37° C. for 4 min. Wash three times with PBS/1% Casein.

4. Dilute goat anti-human IgG Fc peroxidase (Jackson Lab) conjugate 1:50,000 into PBS/1% Casein and incubate 100 µl per well for 30 min 37° C. Wash three times as above.

5. Dilute a 30 mg OPD tablet into OPD substrate buffer (Phosphate/citrate pH 4.5 with $H_2O_2$) to a final concentration of 3 mg/ml. Add 100 µl of substrate to each well and incubate at RT for five minutes.

6. Stop development with 100 µl 1N HCl and read plate at 492 nm.

| Results | |
|---|---|
| SERUM FINAL DILUTION | % INHIBITION* |
| 1/2 | 1.27% |
| 1/10 | 27.5% |
| 1/100 | 45.9% |

* = 1 − [Ratio of absorbance of specimen with HLA antigen divided by absorbance of specimen with negative control]

These results demonstrated that a dose dependent specific inhibition of antibody binding could be obtained.

STUDY 2

Same protocol as above.

| | Serums tested: % Inhibition with soluble HLA B7 | |
|---|---|---|
| | Serum diluted 1:25 | Serum diluted 1:100 |
| Anti-B7 #1 | 36.9% | 55% |
| Anti-B7 #2 | 40.7% | 61.3% |
| Anti-B7 #3 | 48.8% | NT |
| Anti-A2 #1 | 7.1% | 28% |
| Male Normal human serum #4 | 0% | 0% |

It is evident from the above results, that the subject method provides an easy procedure for determining HLA from a wide variety of sources, including soluble and insoluble antigens e.g. surface membrane HLAs. The method is rapid, easily performed, requires readily available reagents, and can be performed with numerous samples determining numerous alleles in a highly efficient manner.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting histocompatibility between a human donor and recipient of a transplant, said method comprising:

preparing at least two samples, wherein each sample is prepared by combining a blood aliquot from said donor and a blood aliquot from said recipient, and wherein differing samples have differing ratios of recipient to donor aliquot volumes, and wherein in each of said samples said aliquot from said recipient is not greater than the volume of said aliquot from said donor, and at least one control lacking said donor blood aliquot;

incubating said samples for sufficient time for any complexes between soluble HLA antigen and IgG anti-HLA antigen to form;

adding each of said samples to a different solid support coated with substantially all of the popular HLA allelic proteins;

determining the amount of IgG antibody bound to each of said solid supports as compared to at least one control, where an increase in the inhibition of IgG antibody bound to the support with a decreasing ratio of recipient to donor aliquot volumes when corrected for the value from the control indicates lack of histocompatibility.

2. A method according to claim 1, wherein said determining comprises:

adding a conjugate of an enzyme and an IgG binding reagent to said support for sufficient time for said IgG binding reagent to bind to any IgG present on said support; and adding substrate and detecting the formation of product from said substrate as a measure of the amount of IgG present on said support.

3. A method according to claim 2, wherein said IgG binding reagent is anti-IgG antibody.

4. A method according to claim 2, wherein said enzyme is horse radish peroxidase.

* * * * *